United States Patent

Kapps et al.

[11] 4,060,571
[45] Nov. 29, 1977

[54] PRODUCTION OF N,N-BIS-(2-HYDROXYALKYL)-AMINOMETHANE PHOSPHONIC ACID DIALKYL ESTERS

[75] Inventors: Manfred Kapps, Leverkusen; Karl-Heinz Mitschke, Odenthal; Reinhard Schliebs, Cologne, all of Germany

[73] Assignee: Bayer Aktiengesellschaft, Leverkusen, Germany

[21] Appl. No.: 656,034

[22] Filed: Feb. 6, 1976

[30] Foreign Application Priority Data

Feb. 15, 1975 Germany .................... 2506442

[51] Int. Cl.$^2$ ............................. C07F 9/40
[52] U.S. Cl. ........................ 260/970; 260/937; 260/945
[58] Field of Search .................. 260/945, 970

[56] References Cited

U.S. PATENT DOCUMENTS 3,297,796   1/1967   Smith et al. .................. 260/945 X Primary Examiner—Anton H. Sutto
Attorney, Agent, or Firm—Burgess, Dinklage & Sprung

[57] ABSTRACT

A process for the production of N,N-bis-(2-hydroxyalkyl)-aminomethane phosphonic acid dialkyl esters of the formula

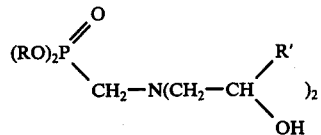

in which
R is an optionally substituted alkyl radical with 2 to 10 carbon atoms, and
R' is hydrogen or a lower alkyl radical with up to 6 carbon atoms,
comprising reacting an oxazolidine of the formula

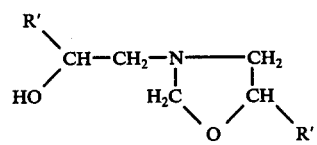

with a dialkyl phosphite in the presence of an acid ion exchanger. Preferably R is ethyl or isopropyl, R' is hydrogen or methyl, the ion exchanger is a sulfonated polystyrene resin and the reaction is effected at about 30° to 120° C, especially 60° to 100° C. The products are thereby obtained rapidly in higher purity than heretofore possible.

5 Claims, No Drawings

PRODUCTION OF N,N-BIS-(2-HYDROXYALKYL)-AMINOMETHANE PHOSPHONIC ACID DIALKYL ESTERS

This invention relates to a process for the production of N,N-bis-(2-hydroxalkyl)-aminomethane phosphonic acid dialkyl esters corresponding to the general formula (I)

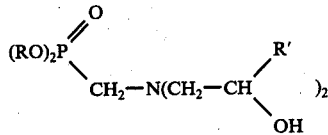

in which
R represents a straight-chain or branched-chain alkyl radical having 2 to 10 carbon atoms which may be unsubstituted or substituted; and
R' represents hydrogen or a lower alkyl radical having up to 6 carbon atoms, by reacting oxazolidines with dialkyl phosphites.

Compounds corresponding to formula I are disclosed in U.S. Patent Specification No. 3,076,010 and are primarily used as fire-retarding additives for polyurethane foams according to German Auslegeschrift No. 1,143,022 and German Offenlegungsschrift No. 1,745,471.

Unfortunately, numerous difficulties are involved in the production of compounds of this type by conventional processes. For example, in the reaction of alkanolamine, formaldehyde and dialkyl phosphites according to German Offenlegungsschrift No. 1,745,471, the desired reaction is accompanied by hydrolysis of the alkoxy groups on the phosphorus atom or by alkylation on the nitrogen atom.

Although no hydrolysis can occur in a process where the oxazolidines are initially formed from alkanolamine and formaldehyde and subsequently reacted with dialkyl phosphites or even with phosphorspiranes, the possibility of undesirable alkylation or transesterification still exists. The reaction velocity between the phosphorus compound and the oxazolidine is very low, especially where sterically demanding radicals are present in the alkanolamine, so that elevated temperatures are required for obtaining useful reaction velocities. Under these conditions, however, the formation of secondary products and decomposition products is promoted to a considerable extent.

The present invention provides a process for the production of N,N-bis-(2-hydroxyalkyl)-aminomethane phosphonic acid dialkyl esters corresponding to the general formula (I)

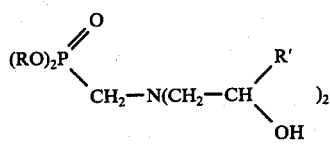

in which
R represents a straight-chain or branched-chain alkyl radical with 2 to 10 carbon atoms which may be unsubstituted or substituted; and
R' represents hydrogen or a lower alkyl radical with up to 6 carbon atoms, by reacting oxazolidines corresponding to the general formula (II)

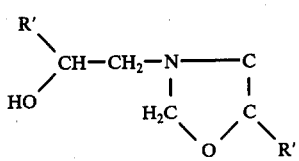

in which
R' has the same meaning as in formula I, with dialkyl phosphites, characterized by the fact that the reaction is carried out in the presence of acid ion exchangers.

It has surprisingly been found that N,N-bis-(2-hydroxyalkyl)-aminomethane phosphonic acid dialkyl esters corresponding to formula I can be obtained in a hitherto unattainable purity in relatively short reaction times if, in accordance with the invention, the reaction is carried out in the presence of catalytic quantities of preferably dried acid ion exchangers.

The process according to the invention may be carried out both continuously (generally in several stages in a reaction cascade) and also in batches. In cases where the process is carried out on the batch principle, one of the two components is initially introduced with the catalyst. The other component, preferably the compound of formula II, is subsequently added. The reaction temperatures range from about 30° to 120° C and preferably range from about 60° to 100° C, depending upon the size of the radicals R and R'. The reaction times are between about 0.1 and 15 hours. In principle, the reaction may be carried out in suitable solvents for example, benzene, toluene, or petroleum ether, although it is preferably carried out in the absence of solvents.

In order to complete the reaction, the reaction mixture is preferably after-heated. The progress of the reaction may be followed by NMR-spectroscopy, the reduction in the P-H-signals of the phosphorus starting components being a measure of the degree of conversion. These signals disappear when the reaction is over. The resulting compounds of formula I are partly viscous, water-soluble substances with a weak alkaline reaction.

In principle, suitable catalysts for the process according to the invention are any known ion exchangers which are present in the acid form and which do not react with the other constituents of the reaction mixture. Thus, suitable materials are materials of which the supports consist of polystyrene or of phenol-formaldehyde resins. The characteristic groups of the ion exchanger may be, for example sulfonic acid, phosphonic acid, arsonic acid or boric acid groups. In addition, however, it is also possible to use inorganic ion exchangers for example, crystalline and/or amorphous aluminosilicates (zeolites, mordenites, Permutits ®) in the H-form.

Preferred catalysts are, for example, acid ion exchangers which have been dried in vacuo at 80 to 110° C, for example the Lewatits ® marketed by Bayer AG. These ion exchangers carry sulfonic acid groups on crosslinked polystyrene resins and are similar in their effect to strong acids such as, for example, $H_2SO_4$. The material may be used in granular or powder form. The ion exchanger is used in an amount between about 0.1 and 10 g and more especially between about 0.3 and 2.0 g per mole of the phosphite. The exchanger resins may be repeatedly reused. Basically, it is also possible, but not economically advisable, to use a larger quantity of exchangers. Neither is it advisable to reduce the quantity of catalyst to less than about 0.1 g/mole of phosphorus compound. Although, in this case, the reaction times are shorter than in the case of reaction carried out in the absence of catalyst, they are still too long for practical purposes, in addition to which the secondary reactions referred to above are again encountered.

The oxazolidines of formula II used are obtained by known methods from bis-($\beta$-hydroxyalkyl)-amines and formaldehyde at temperatures from 40° to 50° C. Before they are used, the compounds of formula I are freed from water in known manner or preferably distilled.

Preferred substituents for R are, for example, $C_2H_5$- and $C_3H_7$-radicals, and, for R', hydrogen or $CH_3$- groups.

The following dialkyl phosphites for example may be used: diethyl phosphite, di-n-propyl phosphite, diisopropyl phosphite, dibutyl phosphite, dipentyl phosphite, dihexyl phosphite, diheptyl phosphite or dioctyl phosphite and their isomers. Diethyl phosphite and diisopropyl phosphite are particularly suitable.

Instead of using dialkyl phosphites, it is also possible to use phosphorspirane compounds corresponding to the general formula

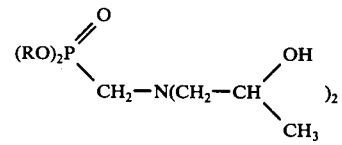

(see German Offenlegungsschrift 2,017,812) and such compounds are embraced by dialkyl phosphites as employed herein. In this case, too, the reaction is accelerated.

The products obtained by the process according to the invention have improved properties in relation to the commercially available products produced by known methods. Thus, in addition to their lighter color (attributable to milder reaction conditions and the modified reaction method wherein the oxazolidines are preferably subsequently added), particular reference is made to the reduced viscosity of the products. This ensures that the foaming process gives improved foams of constant quality. This result is also consistent with spectroscopic observations. Thus, there is no sign of the secondary products ethanol (formed by transesterification) or of foreign phosphite fractions (formed by hydrolysis and alkylating reactions) which occur in conventional processes. These secondary products have an adverse effect upon the foaming process, as confirmed by comparing two compounds of formula I ($R = C_2H_5$; $R = H$) which were produced by a known process and by the process according to the invention, respectively. The high purity of the compound produced by the process according to the invention provides for an intensified catalytic effect by the tertiary amino group (Example 8). As can be seen here, shorter setting and rise times were measured for the same activator concentration. Accordingly, the product obtained by the process according to the invention makes a greater contribution towards catalysis.

With different reactivities of the hydroxyl groups between the highly functional starting polyol and the compounds I and II of low functionality, crack formation occurs in the core zone of hard polyurethane foam blocks of high gross density. Under the intensified catalytic effect of the adjacent amino group, the phosphorus-containing diol preferentially reacts in the initial phase where it contains primary hydroxyl groups (compound I; $R' = H$). In the hardening phase, the foam is slow in reaching a stability sufficient to withstand the stresses attributable to the high foaming temperature.

Surprisingly, the compound of formula I ($R' = CH_3$) obtained by the process according to the invention

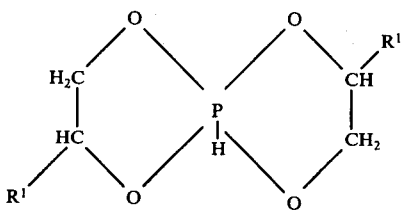

which now contains secondary hydroxyl groups comparable in their reactivity with the polyols, no longer shows any crack formation in the core zone, even with high foam densities (Examples 9 and 10). It was not possible to synthesize compound I ($R' = CH_3$) by the known method, because in that case only acidic unusable products are obtained. It is only the compounds I ($R' = CH_3$) obtained by the process according to the invention which are usable.

The process according to the invention is illustrated by the following Examples:

For the process according to the invention, the standard commercial-grade ion exchangers are dried for 1 to 5 hours at 80° to 100° C under an absolute pressure of approximately 3 mm Hg.

EXAMPLE 1

(Comparison Example, no catalyst added)

29.0 g (0,2 mole) of the distilled oxazolidine of diisopropanolamine and formaldehyde were reacted while stirring at 80° to 90° C with 27.6 g (0.2 mole) of diethyl phosphite. After 7 hours, the P-H-signal of the phosphite (emanating from secondary products) was still noticeable in the NMR. 56 g of a product of the following formula were obtained:

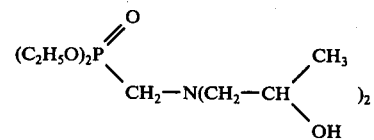

It shows the following features:

| | |
|---|---|
| acid | 5.05 m Mole $H^\oplus$ /100 g of substance |
| water | 0.044 % |
| viscosity | 476 cP |
| density | 1.099 g/ml |
| color | red-brown |

EXAMPLE 2

29.0 g (0.2 mole) of distilled oxazolidine (same as in Example 1) were added while stirring at 90° C to 27.6 g (0.2 mole) of diethyl phosphite and 0.3 g of an acid ion exchanger, a granulated product based on polystyrene resin containing sulfonic acid groups (Lewatit ® SC-104/H) which had been dried under the conditions described above. After 2 hours, the P-H-signal (in the NMR-spectrum) had quantitatively disappeared. The ion exchanger was separated off by means of a frit. 56.5 g of a pure product corresponding to the formula given in Example 1 were obtained. This product was distinguished above all by its acid number of 0 and also by its low viscosity.

The product has the following properties:

| base | 6.22 m Mole of OH⁻/100 g of substance |
|---|---|
| water | 0.06 % |
| viscosity | 250 cP |
| density | 1.096 g/ml |
| color | pale yellow |

In similarly conducted 30 mole reactions, the reaction time again was only 2 hours.

EXAMPLE 3

145.2 g (1 mole) of distilled oxazolidine as in Example 1) were added dropwise at 80° C to 306.4 g (1 mole) of diisooctyl phosphite and 2 g of acid, dired ion exchanger according to Example 2. This was followed by stirring for 4 hours at 100° to 110° C. 450 g of a product corresponding to the formula $$(CH_3-CH-(CH_2)_4-O)_2-P\underset{CH_2-N(CH_2-CH\underset{OH}{\overset{CH_3}{\diagup}})_2}{\overset{\displaystyle\overset{O}{\|}}{\diagdown}}$$
$$\underset{C_2H_5}{|}$$

were obtained following separation of the ion exchanger.

In the absence of a catalyst, reaction times of more than 10 hours are required for reactions with less reactive dialkyl phosphites of this kind.

EXAMPLE 4

234.3 g (2 moles) of oxazolidine (from diethanolamine and formaldehyde) were added dropwise at 55° to 60° C to 276 g (2 moles) of diethyl phosphite and 1 g of acid ion exchanger according to Example 2. The internal temperature was also kept at 65° C during after-heating. The reaction was over after less than 3 hours. The catalyst was separated off in the usual way. The yield amounted to 505 g of a product corresponding to the formula $$(C_2H_5O)_2P\underset{CH_2-N(CH_2-CH_2OH)_2}{\overset{\displaystyle\overset{O}{\|}}{\diagdown}}$$

This product had the following properties:

| acid O, base | 1.59 m Mole OH⁻/100 g of substance |
|---|---|
| water | 0.104 % |
| viscosity | 170 cP |
| density | 1.153 g/ml |
| color | pale yellow |

For comparison, a commercial-grade product produced in accordance with the prior art had the following properties:

| acid | 0.793 m Mole H⁺/100 g of substance |
|---|---|
| water | 0.1 % |
| viscosity | 235 cP |
| density | 1.16 g/ml |
| color | red-brown |

EXAMPLE 5

23.4 g (0.2 mole) of oxazolidine (same as in Example 4) were added dropwise at 70° to 80° C to 61.3 g (0.2 mole) of diisooctyl phosphite and 1 g of acid ion exchanger according to Example 1. The reaction ceased after 3 hours at 85° C. 84 g of a product corresponding to the following formula were obtained following separation of the ion exchanger:

$$(CH_3-CH-(CH_2)_4-O)_2-P\underset{CH_2-N(CH_2-CH_2OH)_2}{\overset{\displaystyle\overset{O}{\|}}{\diagdown}}$$
$$\underset{C_2H_5}{|}$$

EXAMPLE 6

138.1 g (1 mole) of diethyl phosphite and 2 g of Erionit (in the hydrogen form) were heated to 85°–90° C, followed by the addition of 145.2 g (1 mole) of oxazolidine (from diisopropanolamine and formalin). The reaction ceased after 2 hours (as observed by NMR-spectroscopy). Following separation of the catalyst by means of a frit, a product of the formula corresponding to Example 1 was obtained in a quantitative yield.

EXAMPLE 7

69.05 g (0.5 mole) of diethyl phosphite and 1.0 g of an acid polystyrene-based ion exchanger containing phosphonic acid groups were reacted at 85° to 90° C with 72.6 g (0.5 mole) of oxazolidine (from diisopropanolamine and formalin). The reaction ceased after 2.5 hours (as observed by NMR-spectroscopy). A product similar to the product of Example 6 was obtained in a quantitative yield following separation of the catalyst.

EXAMPLE 8

Production of polyurethane foams with products corresponding to the formula $$(C_2H_5O)_2P\underset{CH_2-N(CH_2-CH_2OH)_2}{\overset{\displaystyle\overset{O}{\|}}{\diagdown}} \quad (III)$$

A = III by the known process
B = III by the process according to the invention
Mixture:
85 g of a polyether polyol obtained by propoxylating saccharose (OH-number 380, viscosity (25° C) 13,000 cP)
15 g of product A or product B
1.5 g of a silicon stabilizer based on a polyether siloxane modified with lateral polyether groups
0.5 g of water
0.8 g of triethylamine
30 g of monofluorotrichloromethane
115 g of crude 4,4'-diisocyanatodiphenyl methane The polyether polyol was thoroughly mixed in a cardboard beaker with product A or product B, the additives and the blowing agent, after which the quantity of blowing agent which had volatilized during mixing was replaced, the isocyanate added and the mixture intensively stirred (all the components had been tempered at 20° C ± 0.5° C before mixing). Before the beginning of foaming, the reaction mixture was poured into a mold of packing-grade paper (base area 20 × 20 cm², height 14 cm). The following reaction times were measured:

| Test | Product A | | Product B | |
|---|---|---|---|---|
| | 1 | 2 | 3 | 4 |
| Latent time(s) | 64 | 62 | 60 | 61 |
| Setting time(s) | 350 | 349 | 210 | 211 |
| Rise time(s) | 490 | 485 | 380 | 383 |

Production of polyurethane foam blocks:
Composition:
85 parts by weight of a polyether polyol obtained by propoxylating saccharose (OH-number 470, viscosity (25° C) 35,000 cP)
15 parts by weight of a product corresponding to the formula:

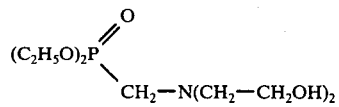

1.5 parts by weight of a silicone stabilizer
0.9 part by weight of triethylamine
22 parts by weight of monofluorotrichloromethane
130 parts by weight of a crude 4,4'-diisocyanatodiphenyl methane A 1 meter wooden cubic box was used as the foaming mold. The inside of the box was coated with wax as release agent. The quantities of reaction mixture were measured in such a way that the blocks reached a height of 80 cm.

Polyol, flameproofing agent, additives and blowing agent were thoroughly mixed in a plastic container, after which the isocyanate was added and the mixture stirred intensively for 40 seconds. The reaction mixture was immediately poured into the prepared mold. In order to avoid a heavily curved foam head, the wooden mold cover was placed loosely on the rising foam at a level of approximately 25 cm and allowed to rise with the foam.

1 Hour after production, the foam blocks were removed from the mold, stored for 3 days and, finally, cut vertically in half. Gross foam density: 53 kg/m³. When the block was cut in half, numerous cracks running perpendicularly of the foaming direction were visible in the core zone.

EXAMPLE 9

In the foaming composition of Example 8, the product of formula I (R' = H) was replaced by the same quantity of the otherwise unchanged product of formula I (R' = CH₃). The composition was otherwise unchanged. Gross foam density: 54 kg/m³. The block did not show any internal cracks.

EXAMPLE 10

The quantity of monofluorotrichloromethane in the foaming recipe of Example 9 was reduced to 18 parts by weight. The composition was otherwise unchanged. A gross foam density of 60 kg/m³ was obtained. Despite this relatively high gross density, the block did not show any internal cracks.

In addition to the foregoing reactants where R was unsubstituted alkyl, the reaction can be effected with alkyl substituted with non-interfering groups such as halogen, e.g. chloro, bromo or fluoro, aryl, e.g. phenyl, cyano, alkoxy, e.g. ethoxy, and the like.

It will be appreciated that the instant specification and examples are set forth by way of illustration and not limitation, and that various modifications and changes may be made without departing from the spirit and scope of the present invention.

What is claimed is:

1. A process for the production of N,N-bis(2-hydroxyalkyl)-aminomethane phosphonic acid dialkyl esters of the formula

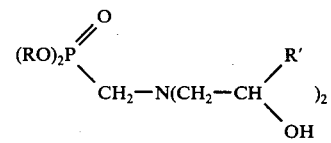

in which
R is an optionally substituted alkyl radical with 2 to 10 carbon atoms, and
R' is hydrogen or a lower alkyl radical with up to 6 carbon atoms,
comprising reacting an oxazolidine of the formula

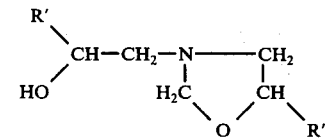

with a dialkyl phosphite in the presence of an acid ion exchanger.

2. A process as claimed in claim 1, wherein the ion exchanger is a resin containing sulfonic acid groups.

3. A process as claimed in claim 1, wherein the reaction is carried out at a temperature of about 30° to 120° C.

4. A process as claimed in claim 2, wherein R' is hydrogen or methyl, the dialkyl phosphite is diethyl or di-isopropyl phosphite, and the reaction is carried out at a temperature of about 60° to 100° C.

5. A process as claimed in claim 3, wherein the reaction is carried out at a temperature of at least about 85° C.

* * * * *